United States Patent [19]

LaBauve

[11] Patent Number: 4,520,808

[45] Date of Patent: Jun. 4, 1985

[54] INHALATION EXPOSURE APPARATUS

[75] Inventor: Raphael J. LaBauve, West Hartford, Conn.

[73] Assignee: Stauffer Chemical Company, Westport, Conn.

[21] Appl. No.: 474,098

[22] Filed: Mar. 10, 1983

[51] Int. Cl.$^3$ ............................................. A61M 15/00
[52] U.S. Cl. ........................ 128/200.14; 128/200.19; 128/203.29; 128/205.25; 128/910
[58] Field of Search ...................... 128/200.19, 203.29, 128/203.12, 205.25, 910, 200.14, 730, 205.19

[56] References Cited

U.S. PATENT DOCUMENTS

| | | | |
|---|---|---|---|
| 2,843,119 | 7/1958 | Glasser | 128/205.25 |
| 3,230,577 | 1/1966 | Hughes | 128/205.25 |
| 3,915,165 | 10/1975 | Rambosek et al. | 128/203.29 |
| 4,332,244 | 6/1982 | Levy et al. | 128/910 |

OTHER PUBLICATIONS

Schmidtke, "Removal of Inhaled Radioactive Yttrium by the Use of Diethylenetriamine–Pentaacetic Acid (DTPA)", Health Physics, Pergamon Press, 1964, vol. 10, pp. 1235-1241, Printed in Northern Ireland.
Lie, "Deposition and Retention of $^{137}C_s$ in the Rat Following Inhalation of the Chloride and the Nitrate", Health Physics, Pergamon Press, 1964, vol. 10, pp. 1071-1076, Printed in Northern Ireland.
Raabe et al., "An Improved System for Exposure of Beagle Dogs to Radioactive Aerosols", Inhalation Toxicology Research Inst. Annual Report, 1972-1973, LF-46, UC-48, Dec. 1973, pp. 10-15.
LaBauve et al., "Cytogenetic and Other Biological Effects of $^{239}PuO_2$ Inhaled by the Rhesus Monkey", Radiat. Res. 82, 310-335 (1980).
Boecker et al., "A Canine Inhalation Exposure Apparatus Utilizing a Whole Body Plethysmograph", Health Physics, Pergamon Press, 1964, vol. 10, pp. 1077-1089.
Craig et al., "Deposition, Translocation and Effects of Transuranic Particles Inhaled by Experimental Animals", Biology Department, Battelle, Pacific Northwest Labs., Richmond, WA 99352, Airbourne Radioactivity (No. 710001), ANS La Grange Park, IL, 1978.

Primary Examiner—Henry J. Recla
Attorney, Agent, or Firm—Hensley M. Flash

[57] ABSTRACT

An inhalation apparatus for exposing small laboratory animals, e.g., rats, to a test atmosphere in such a manner that the animals are exposed to a uniform concentration of the test atmosphere containing substantially no exhaled materials.

The apparatus comprises, e.g., an animal holding tube capable of positioning the nose of an animal at a fixed point within the tube. The tube is provided with a test atmosphere inlet means located in the vicinity of the nose and an exhaust outlet such that the test atmosphere can be inhaled by the animal then exhausted rearward of the nose of the animal.

A plurality of these animal holding tubes can be combined by connecting their inlet to a first plenum duct that is in communication with a source of the test atmosphere and connecting their outlet to a second plenum duct for exhausting substantially all exhaled materials and excess test atmosphere.

19 Claims, 3 Drawing Figures

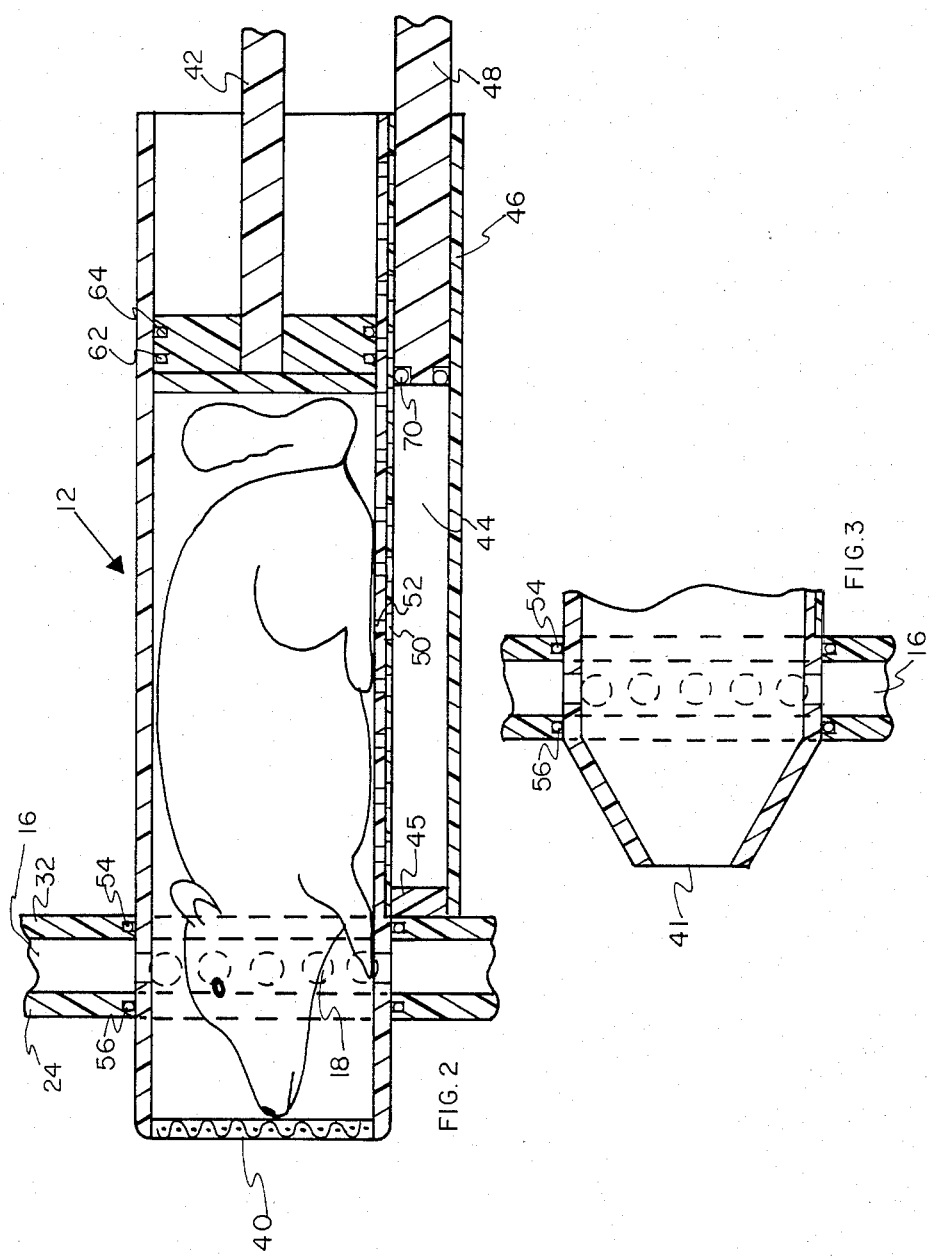

INHALATION EXPOSURE APPARATUS

FIELD OF THE INVENTION

This invention relates to animal research apparatus for exposing laboratory animals to controlled environmental contaminants and, more particularly, to research apparatus useful in inhalation toxicology research, in which small laboratory animals are exposed to toxic aerosols to determine the effects thereof.

BACKGROUND OF THE INVENTION

Modern technology has increased the incidence of a wide variety of compounds in the environment. The effect of exposure to these compounds can be predicted to some degree by toxicological evaluation. Respiratory tract exposure to these compounds is less understood than direct ingestion. A special techlology aimed at increasing our knowledge of respiratory tract exposure has evolved.

Various inhalation exposure apparatus have been developed with the object of providing controlled levels of contaminants to animals in order to assess their impact on these animals. Typically, a plurality of animals is placed in a single exposure chamber into which a test atmosphere is discharged. The animals are usually placed in separate holding cages which are often stacked vertically. This type of arrangement is usually referred to as a whole body exposure technique.

A nose-only inhalation exposure technique offers many advantages over a whole-body exposure technique. The exposure of only the nose of the animal to the test material reduces dermal exposure and gastrointestinal exposure due to grooming of contaminated fur. Dermal exposure and gastrointestinal exposure introduces other experimental variables that often mask the effects of pure inhalation, thereby frustrating the understanding of respiratory tract ingestion. Additionally, the nose-only inhalation exposure technique allows the use of a small size chamber for containing the test atmosphere. This reduction in size enables high concentrations of test materials to be achieved with the use of smaller amounts of test materials. These high concentrations are usually mandated by the evaluation protocols established by the various regulatory agencies such as the Environmental Protection Agency. Reduction in size of the chamber contaminated, reduction in the amount of toxic test material used, and reduced pelt contamination allow easier clean-up and greater safety in handling toxic test materials.

A primary design criterion for inhalation exposure systems used in toxicology testing is that the concentration of test material supplied by the exposure plenum be the same as that concentration at the breathing zone of the test animal. This allows the biological effects observed in test animals to be related to actual concentrations measured in the exposure plenum of these systems. Another prime criterion is that the technique used produces the least amount of stress or other conditions which can alter the biological response of the test animal to the toxic test material.

Many attempts have been made to match these design criteria but no particular design has been found to be completely acceptable. A rubber dam or diaphram fitted around the neck of the animal has been tried. This diaphram is ineffective as it invariably leaks and is difficult to achieve a seal, it is uncomfortable thereby increasing animal stress levels, it is generally hard to use, it needs replacement frequently because the construction material is usually a thin pliable rubber, e.g., latex that tears easily and its prolonged exposure to aerosols, especially those containing oils, promotes rotting or other destruction of the latex.

In the better designs, a major problem has been the ability of the test animal to withdraw its nose from the test material, especially a particularly obnoxious test material, and re-breathe previously exhaled material, rather than fresh test atmosphere. Any re-breathing, whether caused by the test animal withdrawing its nose or by prevously exhaled materials contaminating the supply of test atmosphere, tends to skew test results as exposure concentrations of test materials cannot be determined with any degree of reliability and accuracy.

The present invention overcomes the varied problems of the prior art by providing an apparatus and a method for exposing animals to a test atmosphere in such a manner that the animals are exposed to a uniform concentration of test atmosphere containing substantially no exhaled materials.

SUMMARY OF THE INVENTION

In accordance with the present invention there is provided an inhalation apparatus for exposing small laboratory animals to a test atmosphere comprising an animal holding tube means capable of positioning the nose of an animal at a fixed point within said tube means; said tube means being provided with: test atmosphere inlet means located in the vicinity of said nose; and exhaust outlet means located such that the test atmosphere can be inhaled by the animal then exhausted rearward of said nose of the animal so that said animal is exposed to a uniform concentration of test atmosphere containing substantially no exhaled materials.

The invention further provides a system for exposing several small laboratory animals simultaneously to a test atmosphere comprising in combination: a plurality of the animal holding tube means as recited above; a first plenum duct connecting each tube means located such that a source of the test atmosphere is in fluid communication with the inlet means of each of said tube means; and a secnd plenum duct connecting each tube means and located such that the exhaust outlet means of each tube means is in fluid communication with said second plenum duct so that substantially all exhaled materials and excess test atmosphere can be exhausted. Preferably, an aerosol generator provides the source of the test atmosphere and vacuum means communicates with the second plenum duct for maintaining a negative pressure therein.

The invention further provides a method of exposing the nose of a small laboratory animal to a test atmosphere comprising: holding the animal within a tube such that the nose of the animal is positioned at a fixed point; supplying a test atmosphere in the vicinity of the nose of the animal; and exhausting excess test atmosphere and products of respiration rearward of said nose of the animal after said animal has been allowed to breathe the test atmosphere so that the test atmosphere provided to the nose of the animal contains substantially no exhaled materials.

BRIEF DESCRIPTION OF THE DRAWING

FIG. 2 is a sectional view of an animal holding tube means which can be employed in accordance with this invention.

FIG. 3 is a sectional view of a conical nosepiece.

DETAILED DESCRIPTION OF THE INVENTION

Figure 1:
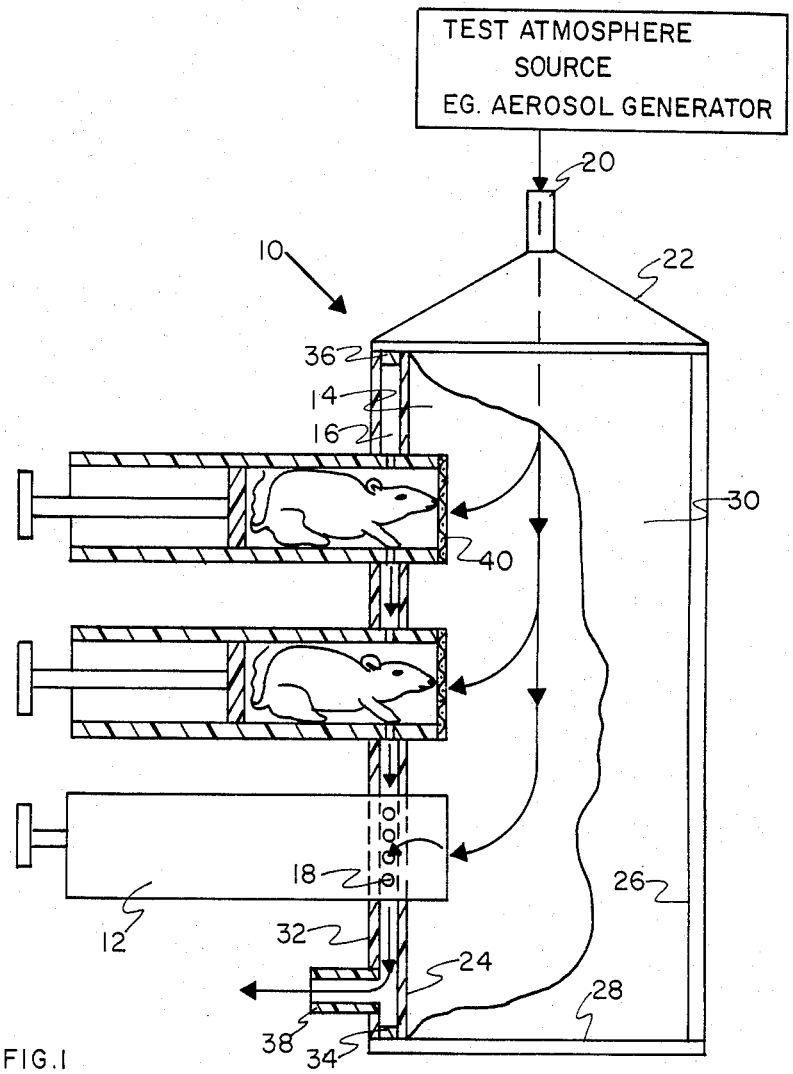
FIG. 1 is a sectional view, partially cut-away, of an animal inhalation exposure system representing one embodiment of the present invention.

FIG. 1 illustrates an animal inhalation exposure system 10 comprising a plurality of animal holding tube means 12, first plenum duct 14, and second plenum duct 16. Exposure system 10 actively draws test atmosphere into animal holding tube means 12, past the nose of the test animal and out through exhaust outlet means 18 into second plenum duct 16. The path of the test atmosphere is outlined in FIG. 1 by the arrows.

Test atmosphere enters first plenum duct 14 by means of inlet 20. The test atmosphere can be supplied by various means, e.g., nebulizers which generate liquid drop aerosols; dust generators; gas generators; gas cylinders; and by exposure to ambient atmospheres occurring either naturally or artificially such as an automobile exhaust or smoke stack emissions. The source of the test atmosphere is preferably an aerosol generator (not shown) which incorporates a test material, usually a toxic chemical, into an aerosol. The aerosol generator can be any of several types, so that a detailed discussion thereof is not believed necessary to a complete understanding of the present invention. In a typical aerosol generator, e.g, the Babbington neubilizer, purified, dry, filtered, compressed air flows through a jet contacting the test material thereby entraining the test material as an aerosol. Once the aerosol is generated, it usually flows next through an aerosol discharger to remove any static electrical charge which can make the aerosol particles stick to each other or the ducting resulting in undesirable reduction in concentration and/or increase in particle size. This conditioned aerosol is the test atmosphere that is conveyed by suitable conduit means to inlet 20.

Inlet 20 can optionally be attached to conical structure 22. The diverging sides of structure 22 facilitates uniform and non-turbulent discharge of the test atmosphere into first plenum duct 14 through inlet 20, as partially illustrated by the arrows. The degree of rise of conical structure 22 is chosen to produce the least turbulence.

In this embodiment of the animal exposure system, first plenum duct 14 is the enclosure defined by walls 24 and 26, conical structure 22, base 28 and surface covering 30 shown partially cut-away. First plenum duct 14 can also be referred to as exposure plenum 14.

Second plenum duct 16 which can also be referred to as exhaust plenum 16 is the enclosure defined by walls 24, 32, 34 and 36. Outlet conduit(s) 38 communicate(s) with the interior of exhaust plenum 16 and is located near the end of said exhaust plenum 16, e.g., furthest from inlet 20. Outlet conduit 38 is connected to a conventional vacuum source (not shown).

FIG. 2 illustrates animal holding tube means 12 that can employed in accordance with this invention. In this embodiment, animal positioning means 42, which can also be referred to as plunger 42, is used to adjust the space within the tube means 12 so that the nose of the test animal is positioned at a fixed point within said tube means 12, i.e., directly adjacent to test atmosphere inlet means 40. Test atmosphere inlet means 40 allows test atmosphere to communicate with the interior of tube means 12. Plunger 42 is not used to actively push the test animal, but only to adjust the inner dimensions of tube means 12. Actively pushing the test animal heightens its stress.

Test atmosphere inlet means 40 is depicted in FIG. 2 as a flat, mesh structure. In FIG. 3, the test atmosphere inlet means is depicted in an alternative embodiment as conical nose-piece 41. The flat mesh structure design allows the test animal more head room decreasing stress levels; however the conical nose-piece positions the nose of the test animal more fixedly. The animals tend to gnaw the conical nose-pieces making them rough and sharp inside. This roughened, rasp-like surface tends to lacerate the animal's lips and thereby increase their stress levels. The flat wire mesh structure cannot be chewed as easily thereby eliminating this problem. However, both designs are capable of adequately functioning as test atmosphere inlet means.

Animal holding tube means 12 depicted in FIG. 2 is further comprised of waste collection means 44. Walls 45 and 46, plunger 48 and the flooring of animal holding tube means 12, define waste collection means 44. Openings 50 and 52 allow waste collection means 44 to communicate with the interior of animal holding tube 12 so that urine and other waste material can flow therefrom and accumulate within said waste collection means 44. Plunger 48 is used to maintain the air-tight integrity of tube means 12. Waste collection means 44 reduces the possibility of the test animal being soaked in its own urine, thereby reducing the stress level of the animal and reducing dermal absorption of test atmosphere.

Exhaust outlet means 18 can be a plurality of exhaust vents located around animal holding tube means 12 in the vicinity of the head of the test animal. At least one such vent is needed to allow the interior of the holding tube means 12 to communicate with exhaust plenum 16 so that excess test atmosphere and other exhaled materials can be exhausted from within holding tube 12.

The walls 24 and 32 of exhaust plenum 16 are preferably fitted with O-ring seals 54 and 56 around the aperture wherein animal holding tube 12 is inserted. These seals assist in maintaining an air tight fit and facilitate the removal and subsequent replacement of animal holding tube means 12, thereby allowing said tube means to be detachable. O-ring seals 62 and 64 assist in maintaining an air tight fitted plunger 42. Similarly O-ring seal 70 assists in maintaining an air tight fitted plunger 48. Rubber collars can work as well as O-ring seals.

The plurality of animals holding tube means are preferably arranged in a spaced relationship, such as a staggered pattern with from about one-half inch to one and one-half inch between each tube means, within walls 24 and 32 of exhaust plenum 16 such that there is at least some space between each tube means to facilitate air circulation thereby reducing heat build-up. A fan can be used to enhance air circulation.

The materials used to construct the apparatus of this invention are preferably as inert as possible to the test materials. Various glasses, plastics and metal alloys are usually the materials of choice.

The path of the test atmosphere as outlined by the arrows in FIG. 1 is as follows: test atmosphere enters exposure plenum 14 via inlet 20; then said test atmosphere is actively drawn into animal holding tube means 12 via test atmosphere inlet means 40 by the pull of the vacuum source connected to outlet conduit 38; and finally the test atmosphere is exhausted from animal holding tube means 12 into exhaust plenum 16 via exhaust outlet means 18 by the pull of the vacuum source. The flow of the test atmosphere can additionally be effected by the push of the pressure at inlet 20 or by the maintenance of a pressure differential between inlet 20 and outlet conduit 38, or by a combination of these various means. In a preferred embodiment a vacuum source is used to pull the test atmosphere through the system. In being exhausted via exhaust outlet means 18, the test atmosphere flows rearward of the nose and preferably across at least the head of the test animal in such a manner that said animal can inhale a constantly changing, fresh supply of test atmosphere that can be representative of a uniform concentration of test atmosphere entering exposure plenum 14 via inlet 20. Substantially all exhaled materials are also pulled out of animal holding tube means 12, into exhaust plenum 16 via exhaust outlet means 18 by the vacuum source. The flow of both test atmosphere and exhaled materials is substantially one way, going from test atmosphere inlet means 40 or the nose of the test animal respectively, then preferably across the head to exhaust outlet means 18, through said outlet and into exhaust plenum 16. For this reason, the test animal cannot re-breathe exhaled materials in preference to the usually more obnoxious test materials and, further, dermal exposure of the test animal is minimized, with only the portion of the test animal located between test atmosphere inlet means 40 and exhaust outlet means 18, being effectively exposed to said test atmosphere. The dimensions of animal holding tube means are selected to minimize the distance between test atmosphere inlet means 40 and exhaust outlet means 18 while fixedly positioning the nose of the test animal between both means with the minimum stress to the animal.

Exhaled materials and excess test atmosphere, i.e., test atmosphere not inhaled by the test animal, flows through exhaust outlet means 18, into exhaust plenum 16 and out of outlet conduit 38 without entering any subsequent animal holding tube means. In this manner, subsequent holding tube means are neither contaminated nor affected in any way by these previously used materials.

The animals used in toxicological testing, and especially in an inhalation exposure apparatus such as that disclosed in the present invention, are usually small laboratory animals such as rats, mice, hamsters, cats, guinea pigs, gerbels and rabbits. Other types of animals can be tested in the apparatus and system of the present invention but the present invention is especially adapted to small laboratory animals such as listed above. These small laboratory animals are neither restrained nor fettered. The nose of the animals are kept at an approximately fixed point because of the dimensions of the holding tube means. The animals are not held rigidly fixed and sedation is not used. For these reasons, stress levels of the test animals are reduced.

The following experimental example demonstrates the effectiveness of the inhalation exposure apparatus of this invention as compared to one of the better known systems of the prior art.

EXPERIMENTAL EXAMPLE

The mortality of Sprague-Dawley derived rats exposed to ammonia for four (4) hours was measured. The rats were divided into two groups for testing. The first group of rats were held individually in animal holding tubes of the type disclosed in the article, "A Method for Chronic Nose-only Exposures of Laboratory Animals to Inhale Fibrous Aerosols" By David M. Smith et al., proceedings of the Inhalation Toxicology and Technology Symposium sponsored by Upjohn Co., Kalamazoo, Mich., Oct. 23 and 24, 1980; ISBN 0250-40414-1; Pgs. 89 to 105; edited by Basil K. J. Leong, Ann Arbor Science Publishers Inc. 1981. These animal holding tubes are fitted with conical nose-pieces for conventional nose-only exposure. The second group of rats were held individually in holding tubes prepared in accordance with the invention. These tubes were similar to the first set but were modified by providing them with exhaust outlet means in the form of a plurality of exhaust vents. These vents were holes of about ⅛" in diameter drilled around the circumference of each tube in the vicinity of the neck of the rat.

Both of these groups of rats were placed in their respective tubes and these tubes were placed at the same time within the exposure plenum of an inhalation exposure apparatus similar to the one depicted in FIG. 1.

The following Table summarizes the results:

TABLE 1

| Mortality of Rats Exposed to $NH_3$ for 4 Hours | | | | | | |
|---|---|---|---|---|---|---|
| Exposure Plenum | Number of Rats Dead/Total Exposed | | | | | |
| $NH_3$ Conc. | Males | | Females | | Total | |
| ppm | I | II | I | II | I | II |
| 4900 | 1/5 | 4/5 | 0/5 | 3/5 | 1/10 | 7/10 |
| 5000 | 0/10 | 7/10 | — | — | — | — |
| 5200 | — | — | 2/10 | 8/10 | — | — |
| 5800* | 2/5 | 3/5 | 3/5 | 3/5 | 5/10 | 6/10 |

*Failure of cooling fan resulted in elevated temperature during the first hour of exposure.
I Indicates the first group of rats held in conventional nose-only tubes.
II Indicates the second group of rats held in modified tubes having exhaust vents.

These results demonstrate the decreased mortality rate for the first group of rats held in conventional nose-only tubes as compared to rats held in modified tubes having exhaust vents. This decreased mortality is due to reduced concentrations of test atmosphere at the breathing zone of the rats caused by the rebreathing of expired air which is reduced in $NH_3$ concentration. More uniform control of test atmosphere inhaled by the test animals produces a more accurate indication of toxicity of the test atmosphere.

Inasmuch as the present invention is subject to many variations, modifications and detail changes, a number of which have been expressly stated herein, it is intended that all matters described within this entire specification or depicted in the accompanying drawings be interpreted as merely illustrative and not limiting.

What is claimed is:

1. An inhalation apparatus for exposing small laboratory animals to a test atmosphere comprising an animal holding tube means capable of positioning the nose of an animal at a fixed point within said tube means, said tube means totally enclosing the animal while allowing free movement of the animal within a space enclosed by the tube means without otherwise fettering said animal, said tube means being further provided with:
   (a) test atmosphere inlet means located in the vicinity of said nose; and
   (b) exhaust outlet means located such that the test atmosphere can be inhaled by the animal then exhausted rearward of said nose of the animal so that said animal is exposed to a uniform concentration of test atmosphere containing substantially no exhaled materials.

2. The apparatus as recited in claim 1, in which the inlet means is a conical nose-piece fitted to the end of said tube means such that the nose-piece converges outwardly from the tube means.

3. The apparatus as recited in claim 1, in which the inlet means is a mesh which closes the end of the tube means.

4. The apparatus as recited in claim 1, in which said tube means further comprises means for positioning the animal within said tube means.

5. The apparatus as recited in claim 4, in which said tube means further comprises a waste collection means connected below the tube means.

6. The apparatus as recited in claim 1, in which said tube means further comprises a waste collection means connected below the tube means.

7. The apparatus as recited in claim 1, in which the exhaust outlet means is at least one exhaust vent located on the tube in a position rearward of the nose of the animal.

8. A system for exposing several small laboratory animals simultaneously to a test atmosphere comprising in combination:
(a) a plurality of animal holding tube means as recited in claim 1;
(b) a first plenum duct connecting each tube means such that a source of the test atmosphere is in fluid communication with the inlet means of each of said tube means; and
(c) a second plenum duct connecting each tube means and located such that the exhaust outlet means of each tube means is in fluid communication with said second plenum duct so that substantially all exhaled materials and excess test atmosphere can be exhausted.

9. The system as recited in claim 8, in which said tube means further comprises means for positioning the animal within said tube means.

10. The system as recited in claim 9, in which said tube means further comprises a waste collection means connected below the tube means.

11. The system as recited in claim 8, in which said tube means further comprises a waste collection means connected below the tube means.

12. The system as recited in claim 8, in which said tube means is detachable.

13. The system as recited in claim 8, in which the source of the test atmosphere is an aerosol generator, said aerosol generator comprising a source of gas under pressure, means for conducting said gas to said inlet means and means for directing a test material into the path of said gas for entraining said test material so that the test atmosphere is formed.

14. The system as recited in claim 13, in which the second plenum duct is in communication with vacuum means for maintaining a negative pressure within said second plenum duct.

15. The system as recited in claim 8, in which the second plenum duct is in communication with vacuum means for maintaining a negative pressure within said second plenum duct.

16. A method of exposing the nose of a small laboratory animal to a test atmosphere comprising:
(a) holding the animal within a tube such that the nose of the animal is positioned at a fixed point and the animal is totally enclosed, while allowing the animal free movement within the tube without otherwise fettering the animal;
(b) supplying a test atmosphere in the vicinity of the nose of the animal; and
(c) exhausting excess test atmosphere and products of respiration rearward of said nose of the animal after said animal has been allowed to breathe the test atmosphere so that the test atmosphere provided to the nose of the animal contains substantially no exhaled materials.

17. The method as recited in claim 16, in which the step of supplying a test atmosphere comprises:
conducting a source of gas under pressure towards the tube; and
directing a test material into the path of said gas for entraining said test material so that the test atmosphere is formed.

18. The method as recited in claim 17, in which the step of exhausting excess test atmosphere and products of respiration comprises vacuuming.

19. The method as recited in claim 16, in which the step of exhausting excess test atmosphere and products of respiration comprises vacuuming.

* * * * *